United States Patent [19]
Laub

[11] Patent Number: 5,944,751
[45] Date of Patent: Aug. 31, 1999

[54] VIBRATORY HEART VALVE

[75] Inventor: Glenn W. Laub, Lawrenceville, N.J.

[73] Assignee: Zertl Medical, Inc., Lawrenceville, N.J.

[21] Appl. No.: 08/123,639

[22] Filed: Sep. 17, 1993

[51] Int. Cl.[6] ........................................................ A61F 2/24
[52] U.S. Cl. .................................................................. 623/2
[58] Field of Search ................................... 128/715; 623/2

[56] References Cited

U.S. PATENT DOCUMENTS

| 4,458,693 | 7/1984 | Badzinski et al. | 128/715 |
| 4,712,565 | 12/1987 | Katz et al. | 128/715 |
| 4,888,009 | 12/1989 | Lederman et al. | 623/2 |
| 4,892,540 | 1/1990 | Vallana | 623/2 |
| 5,052,934 | 10/1991 | Carey et al. | 128/660.01 X |

Primary Examiner—Michael J. Milano
Attorney, Agent, or Firm—Titus & McConomy LLP

[57] ABSTRACT

An implantable heart valve having an oscillator for resonating the valve to prevent clotting.

5 Claims, 2 Drawing Sheets

VIBRATORY HEART VALVE

FIELD OF INVENTION

The invention relates to a novel heart valve and, in particular, to heart valves having positional perturbation means to avoid stagnation and coagulation of the blood.

BACKGROUND OF INVENTION

The present invention relates prosthetic heart valves used as a replacement for a defective natural heart valve. Generally, two types of valves are used for such replacement; a mechanical valve typically made from metals, plastic or ceramic material and a tissue valve made from biological materials such as from animals or humans. Mechanical valves have the advantage of being relatively long lasting but the nonbiological materials can promote the formation of thrombus in the valve and possible blood clots. Tissue valves, on the other hand, are relatively impervious to the formation of clots, but tend to deteriorate over time.

Because of their durability, mechanical valves would be the valve of choice in all cases except that they require the patient to take anticoagulants for life. Anticoagulants have numerous disadvantages and require extensive and life long blood monitoring. Failure to take the anticoagulant can result in the eventual formation of thrombus in the valve itself and embolisms if the clots break off.

Accordingly, it is highly desirable to find a means or method which takes advantage of mechanical heart valves without the life long requirement for the patient to take anticoagulants. Thus, it is an object of the present invention to provide a heart valve means which has the advantage of both mechanical and tissue valves. It is a further object of the present invention to provide means which can be incorporated into or onto a conventional mechanical heart valve which reduces the formation of thrombus or embolisms. It is a further object of the invention to provide a mechanical heart valve which enhances blood flow over the surface of the valve without stagnation.

SUMMARY OF THE INVENTION

Generally, the present invention comprises a means for enhancing blood flow over the surface of a heart valve. In a preferred embodiment, means for imparting a pulsating or vibrating movement to the valve is provided to increase blood flow over certain portions of the valve surface. It is contemplated that such pulsation or vibration disturbs the stagnation of blood over the valve surface to prevent blood coagulation and thrombus formation.

In one embodiment, oscillation means are incorporated into the valve housing. A crystal oscillator is mounted to the housing and connected electrically to means inside or outside the body for supplying controlled electrical current. Alternatively, oscillation means can be integrated into the valve itself or housing. Crystal oscillators can also be mounted externally to existing valves and valve housings and connect thereto by a wave guide or other coupling means.

Preferably, the vibratory or pulsating motion imparted to the valve is continuous, but noncontinuous motion can be imparted on a regular cyclic basis, e.g. once a minute. The electrical supply and control means for activating the impaction of motion is housed within the body in much the same form as a cardiac pacemaker or implantable detibrillator. In a discontinuous mode, activation control can be either programmable or fixed. Other advantages of the present invention will become apparent from a perusal of the following detailed description of presently preferred embodiments taken in connection with the accompanying drawings.

PRESENTLY PREFERRED EMBODIMENTS

Figure 1:
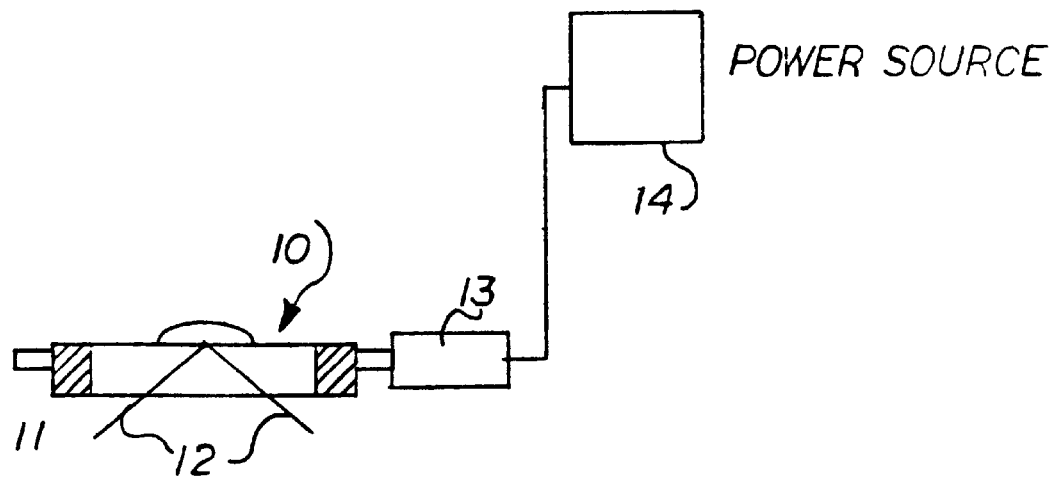
FIG. 1 is a diagrammatic view of a heart valve and housing therefor having a means for vibrating the housing in accordance with the present invention.

Referring to FIG. 1, a conventional mechanical heart valve 10 having a housing 11 and valve 12 is shown. Either a bileaflet (as shown) or single leaflet type valve is suitable and preferred for use in the invention. Other types of valves are suitable as well. An electromechanical means 13 is mounted to heart valve housing 11 and connected to a sealed powered supply and controller 14.

Various types of electromechanical and piezoelectrical devices and oscillators are suitable. PZT ceramic crystal oscillators are a preferred example of the type of oscillator which is suitable for use. In selecting the appropriate oscillator, the amount and type of vibratory energy sufficient to mix the blood and to prevent any pooling of blood on the valve itself is required.

Generally, it is contemplated that a resonance frequency of 10 hz to 50 K $H_z$ is suitable. Other preferred frequency ranges can be used and are dependent to a large measure on the dynamics and material of the heart valve and housing. Also, of importance is the mass dynamics of the valve when the vibratory means is mounted directly or incorporated thereto. Small crystal oscillators of low mass do not effect the performance of the valve, but care in lead connection and mounting becomes critical. Thus, it is preferred to mount the vibratory means on the housing so as to minimize or avoid the problem associated with valve performance.

Figure 2:
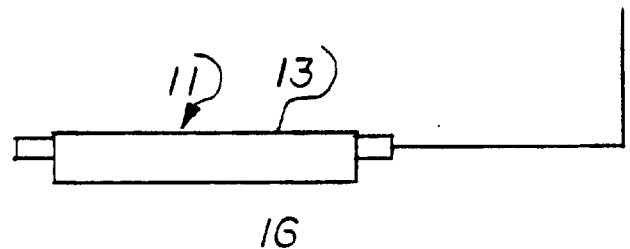
FIG. 2 is a diagrammitc view of a heart valve housing with an integrated vibratory means.
Figure 3:
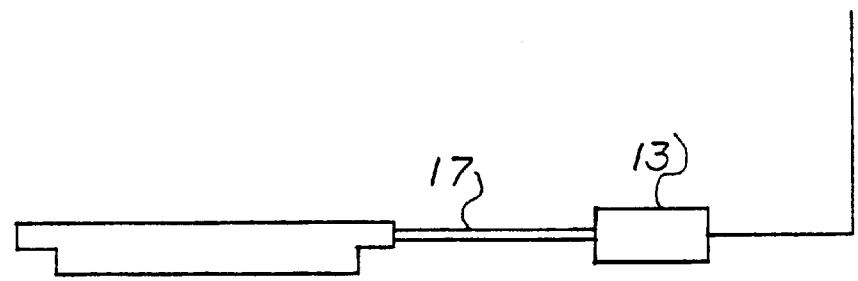
FIG. 3 is a diagrammatic view of a heart valve connected to a vibratory means by a mechanical coupling.

With reference to FIG. 2, an electromechanical oscillator 16 is built into the housing 11. This embodiment has the advantage of simplified replacement during the operating procedure, but is suitable only for newly designed or configured heart valves. In the embodiment shown in FIG. 3, a coupler 17 or waveguide is used to direct the oscillating energy to housing 11 from oscillator 13. This embodiment is suitable for valve implants that do not accommodate the use of integrally or directly mounted oscillators.

Figure 4:
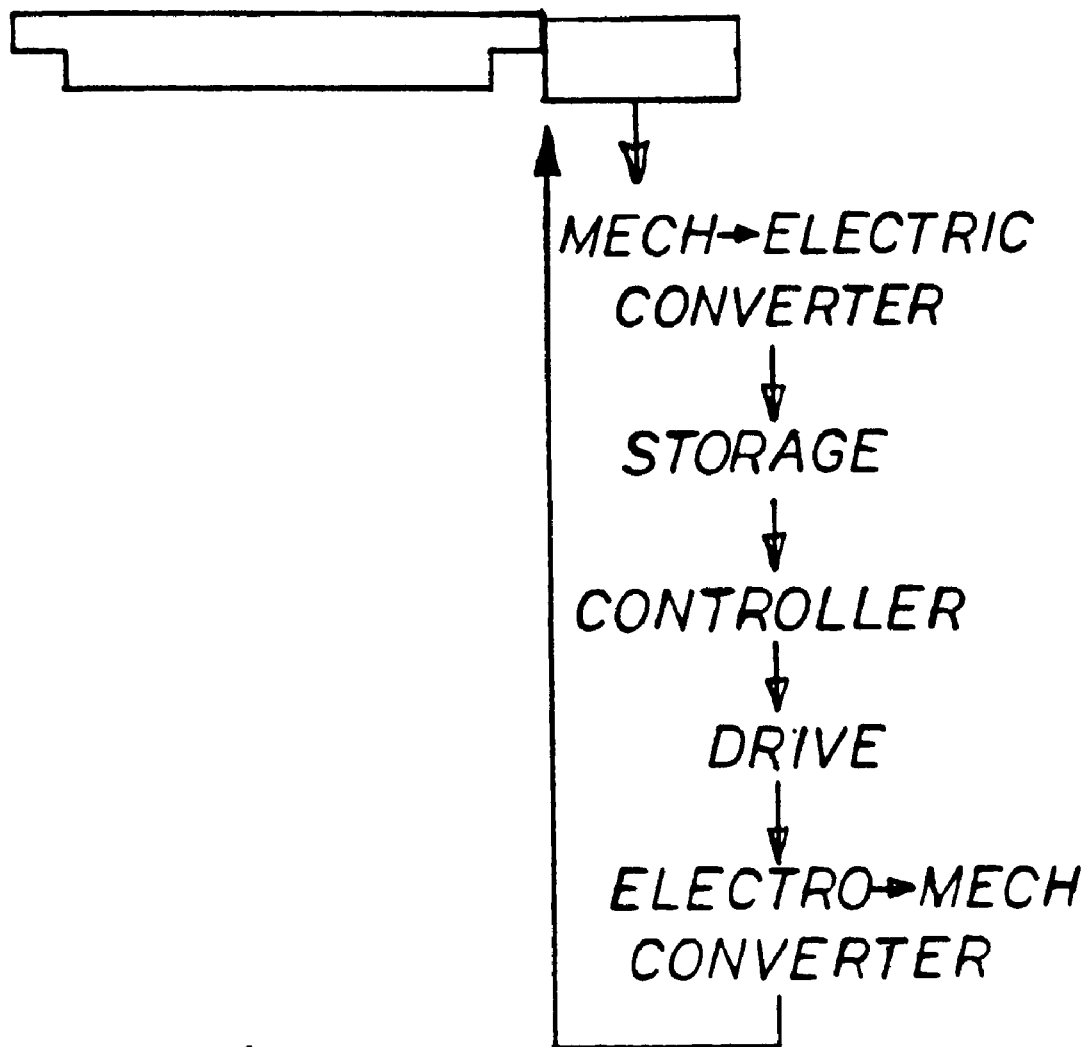
FIG. 4 is a diagrammatic view of a means converting energy from a heart valve to energize an integral means for vibrating the heart valve.

In another embodiment, FIG. 4, the energy developed by movement of valves 12 is used to generate a small current through piezoelectric means 18 or microgenerator which is stored in a storage mean, such as a capacitor or battery 19 and slowly released to power the oscillator 13. This embodiment is especially beneficial where a noncontinuous oscillator or vibratory motion is to be imparted. In this example, sufficient time between pulses permits recharging of the battery or capacitor to supply enough electrical energy for a short pulse period. Higher frequencies of pulsation or continuous vibratory energy utilization requires supplemental power.

The power supply used in the present invention is preferably a lithium halide battery used in cardiac pacers device.

The electronic controls will depend upon the design characteristics to be employed, but generally will require only minimal elements preferably built on a semiconductor chip for reliability.

While presently preferred embodiments have been shown and described in particularity, the invention may be otherwise embodied within the scope of the appended claims.

What is claimed is:

1. An implantable prosthetic heart valve comprising of a valve housing, at least one leaflet mounted within said housing for permitting and stopping blood flow therethrough and an oscillator for oscillating said leaflet.

2. An implantable prosthetic heart valve as set forth in claim 1 wherein said oscillator is mounted externally of said valve housing.

3. An implantable prosthetic heart valve as set forth in claim 1 wherein said oscillator is integrally mounted with said valve housing.

4. An implantable prosthetic heart valve as set forth in claim 1 wherein said oscillator is operably connected to said leaflets.

5. An implantable prosthetic heart valve as set forth in claim 1 including means for generating electrical energy connected to said leaflets.

* * * * *